US007886602B2

(12) United States Patent
Lopatin et al.

(10) Patent No.: US 7,886,602 B2
(45) Date of Patent: Feb. 15, 2011

(54) APPARATUS FOR DETERMINING AND/OR MONITORING A PROCESS VARIABLE

(75) Inventors: Sergej Lopatin, Lörrach (DE); Helmut Pfeiffer, Steinen (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 537 days.

(21) Appl. No.: 10/591,297

(22) PCT Filed: Mar. 2, 2005

(86) PCT No.: PCT/EP2005/050906

§ 371 (c)(1),
(2), (4) Date: Jun. 22, 2007

(87) PCT Pub. No.: WO2005/085770

PCT Pub. Date: Sep. 15, 2005

(65) Prior Publication Data

US 2007/0277608 A1     Dec. 6, 2007

(30) Foreign Application Priority Data

Mar. 5, 2004   (DE)   ................... 10 2004 011 377

(51) Int. Cl.
*G01N 29/00*  (2006.01)
*H01L 41/04*  (2006.01)
*H01L 41/08*  (2006.01)

(52) U.S. Cl. .................. 73/584; 73/1.83; 73/579; 310/319; 310/321

(58) Field of Classification Search .............. 73/579, 73/597, 290 V, 290 R, 861.356, 861.357, 73/861.38, 864.24, 864.25; 310/38–321, 310/333, 340, 348; 177/187
See application file for complete search history.

(56) References Cited

U.S. PATENT DOCUMENTS

| 3,170,094 A |   | 2/1965  | Roth |  |
| 3,378,794 A |   | 4/1968  | Traub |  |
| 3,385,104 A |   | 5/1968  | Banks |  |
| 4,633,119 A |   | 12/1986 | Thompson |  |
| 4,740,726 A |   | 4/1988  | Umezawa |  |
| 4,756,197 A | * | 7/1988  | Herzl | ............... 73/861.355 |
| 5,408,168 A | * | 4/1995  | Pfandler | ................. 318/642 |

(Continued)

FOREIGN PATENT DOCUMENTS

DE     38 08 481 C2     9/1989

(Continued)

*Primary Examiner*—Jacques M Saint Surin
(74) *Attorney, Agent, or Firm*—Bacon & Thomas, PLLC

(57) ABSTRACT

An apparatus for determining and/or monitoring at least one physical or chemical, process variable of medium having at least one oscillatable unit, which produces, and/or receives, mechanical oscillations. Included is at least one tuning unit, whose stiffness is changeable and which is embodied in such a manner and connected in such a manner with the oscillatable unit, or is a part of the oscillatable unit in such a manner, that at least the resonance frequency of the oscillatable unit is changeable via the tuning unit. A corresponding method is also noted.

6 Claims, 2 Drawing Sheets

U.S. PATENT DOCUMENTS

| | | | |
|---|---|---|---|
| 5,531,126 A | 7/1996 | Drahm | |
| 6,644,116 B2 * | 11/2003 | Getman et al. | 73/290 V |
| 6,684,716 B2 * | 2/2004 | Ohnishi et al. | 73/861.357 |
| 6,840,109 B2 * | 1/2005 | Drahm et al. | 73/650 |
| 6,948,379 B2 * | 9/2005 | Hussain et al. | 73/861.357 |
| 7,017,424 B2 * | 3/2006 | Rieder et al. | 73/861.355 |
| 7,036,355 B2 * | 5/2006 | Drahm et al. | 73/54.41 |
| 7,040,181 B2 * | 5/2006 | Rieder et al. | 73/861.357 |
| 7,077,014 B2 * | 7/2006 | Rieder et al. | 73/861.357 |
| 7,162,915 B2 * | 1/2007 | Drahm et al. | 73/54.24 |
| 7,168,315 B2 * | 1/2007 | Ohmayer et al. | 73/290 V |
| 7,168,329 B2 * | 1/2007 | Bell et al. | 73/861.355 |
| 7,191,667 B2 * | 3/2007 | Wenger et al. | 73/861.357 |
| 7,284,449 B2 * | 10/2007 | Rieder et al. | 73/861.356 |
| 7,296,484 B2 * | 11/2007 | Rieder et al. | 73/861.356 |
| 7,353,717 B2 * | 4/2008 | Rieder et al. | 73/861.351 |
| 7,357,039 B2 * | 4/2008 | Rieder et al. | 73/861.357 |
| 7,360,452 B2 * | 4/2008 | Rieder et al. | 73/861.355 |
| 7,360,453 B2 * | 4/2008 | Rieder et al. | 73/861.357 |
| 7,403,127 B2 * | 7/2008 | Pfeiffer | 340/613 |
| 7,436,100 B2 * | 10/2008 | D'Angelico et al. | 310/319 |
| 7,472,607 B2 * | 1/2009 | Bitto et al. | 73/861.357 |
| 7,475,603 B2 * | 1/2009 | Bitto et al. | 73/861.357 |
| 7,490,521 B2 * | 2/2009 | Bitto et al. | 73/861.357 |
| 7,552,634 B2 * | 6/2009 | Huber et al. | 73/290 V |
| 2002/0101253 A1 | 8/2002 | Pletner | |

FOREIGN PATENT DOCUMENTS

| | | |
|---|---|---|
| DE | 197 39 877 A1 | 3/1999 |
| FR | 1 408 436 | 8/1965 |
| RU | 2077036 | 4/1997 |
| WO | WO 94/14047 A1 | 6/1994 |

* cited by examiner

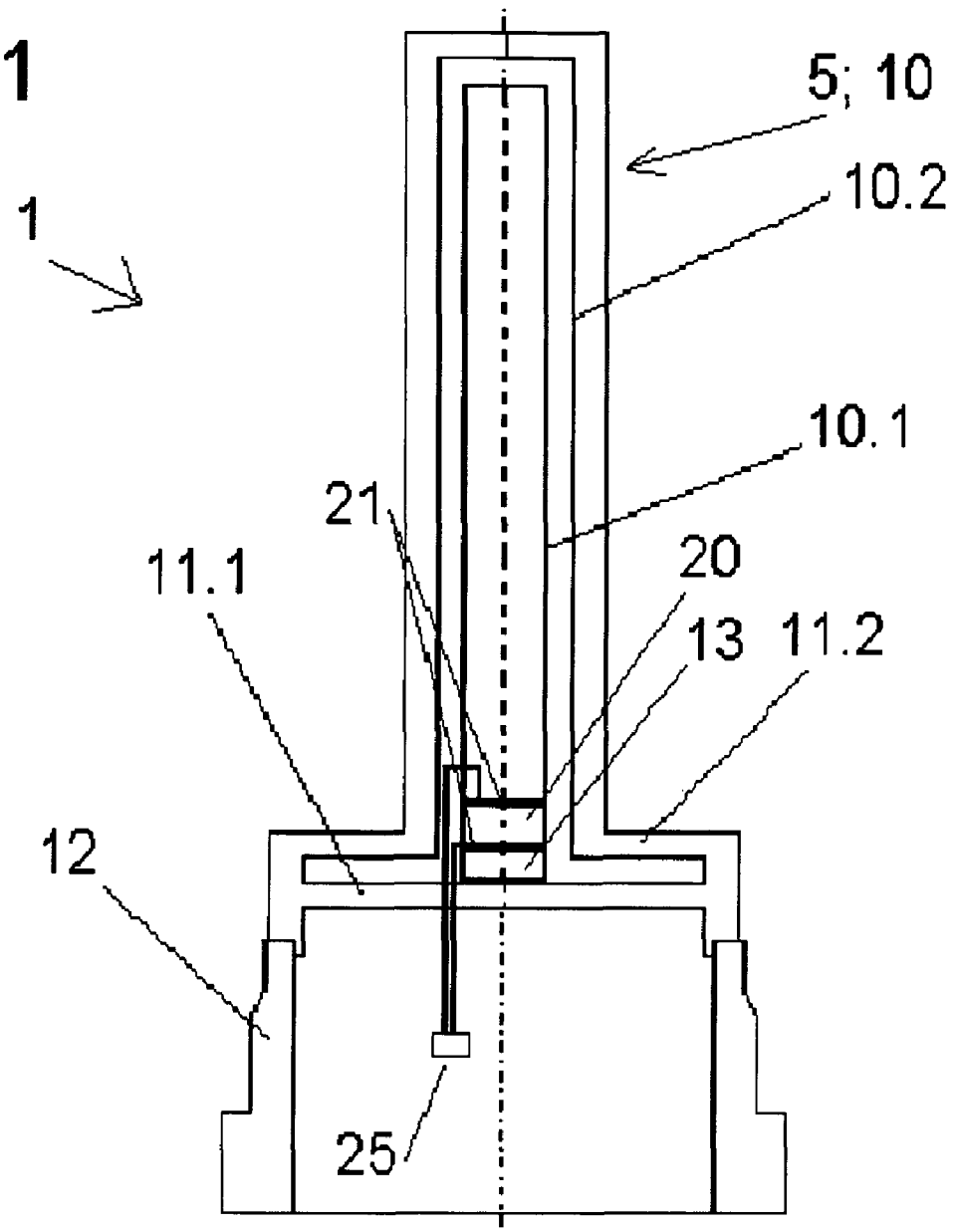

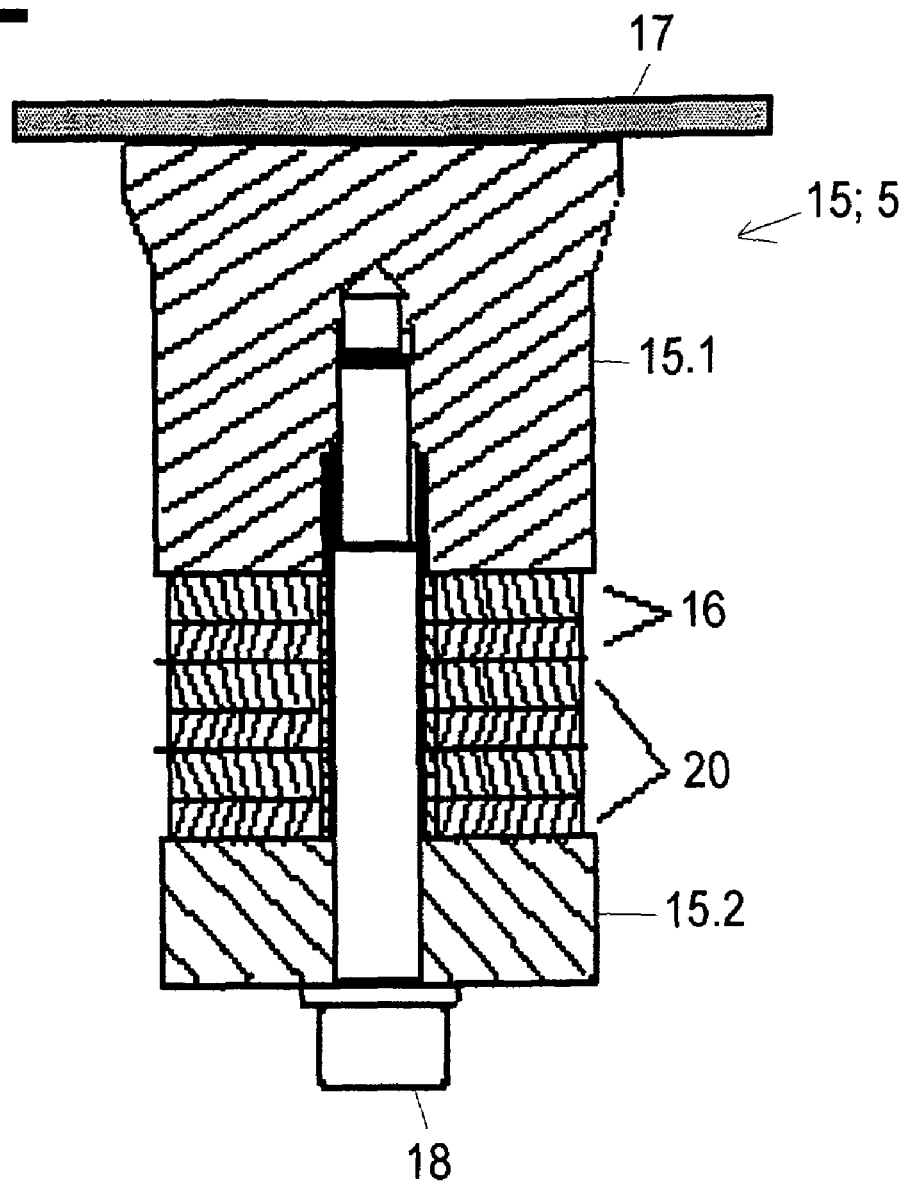

APPARATUS FOR DETERMINING AND/OR MONITORING A PROCESS VARIABLE

FIELD OF THE INVENTION

The invention relates to an apparatus for determining and/or monitoring at least one physical or chemical, process variable of a medium. The apparatus includes at least one oscillatable unit, which produces mechanical oscillations and/or receives them. The process variable can be, for example, the fill level, density or viscosity of a medium in a container or the volume or mass flow of a fluid flowing through a pipe. The oscillations can be produced either continuously or they can be oscillatory packets, so-called bursts.

BACKGROUND OF THE INVENTION

The term "oscillatable unit" is intended to mean a unit which produces and/or receives mechanical oscillations, with the oscillations depending on certain variables predetermined by the unit itself. Such oscillatable units are known, for example, in the form of oscillatory rods, or oscillatory forks, for fill-level limit-detection or in the form of an oscillatory membrane of an ultrasonic transducer, or in the form of a measuring tube of a measurement pickup of vibration-type inserted into the course of a pipeline. Measurement pickups of vibration-type are used, for example, for measuring the mass flow, a density and/or a viscosity of a fluid flowing in a pipeline. In the case of such oscillatable units, the frequency, or wavelength, depends e.g. on inertia and stiffness, when the unit is an oscillatory rod, or on the predetermined velocity of sound in the unit and is likewise influenced by stiffness, when the unit is an ultrasonic transducer. A problem of such oscillatable units is that they must be tuned to certain frequencies, or wavelengths, in order to be usable for certain media or in order to be able to make use of certain advantageous frequency ranges. Furthermore, also most often the corresponding evaluation units, with reference to the used electronics, are designed for particular frequency ranges. In the face of this, the fact remains that the process conditions existing in the application have effects on the tuned resonance frequency, so that such also can be influenced or changed. In the case of so called single-rods (and also, in general, in the case of sensors which come in direct contact with the medium to be measured), the material can e.g. acquire accretions or experience corrosion. Both of these change the mass, and, consequently, also the resonance frequency of the single-rod. In the case of ultrasonic sensors, the resonance characteristics are changed e.g. by the process temperature. Thus, there are process conditions which can nullify the calibration or tuning to the desired frequency.

SUMMARY OF THE INVENTION

Therefore, it is an object of the invention to enable that at least one oscillatory characteristic of an apparatus for determining and/or monitoring a process variable is variably tunable, or matchable, as the case may be.

The object is achieved, with reference to the apparatus, by the provision of at least one tuning unit whose stiffness is changeable and which is embodied in such a manner and connected with the oscillatable unit in such a manner, or is a component of the oscillatable unit in such a manner, that at least the resonance frequency of the oscillatable unit is changeable via the tuning unit. A basic idea of the invention is to use the stiffness of the tuning unit and, consequently, depending on the connection with the oscillatable unit, the stiffness of the oscillatable unit, suitably to tune the resonance frequency and, as required, to adjust in accordance with the application, i.e., in accordance with the process. Therefore, on the one hand, a calibration is possible, which is necessary e.g. due to manufacturing reasons, this, in turn, permitting a larger tolerance for the components, such being relevant for the manufacturer. On the other hand, a calibration or matching can also be done during the application, as may become necessary due to the existing process conditions. Consequently, also in the field and under difficult conditions, the optimal sensitivity can again be set. Furthermore, by targeted changing of the resonance frequency, a predictive maintenance program can be enabled. The tuning unit can in such case be a component of the oscillatable unit or the oscillatable unit and the tuning unit can also be identical, so that one unit assumes both functions. The construction of the tuning unit depends in such case on the type of application and the embodiment of the oscillatable unit.

[An embodiment provides that the tuning unit is made of a piezoelectric material, which is connected with electrodes and whose stiffness is changeable at least by an electric current between the electrodes. The stiffness of the piezoelectric elements can be changed by attaching electrodes which are either free, in which case no current flows between them, or they are short-circuited, in which case a current does flow between the electrodes. In the short-circuited case, the stiffness of the elements is usually lowest. By gradual transitioning between these two states, the stiffness can be gradually changed. With reference to the relative stiffness of a piezoelectric element, differences up to 25% can be achieved. Depending on what fraction of the stiffness of the oscillatable unit comes from the piezoelectric element, the total stiffness and thus the resonance frequency can be changed and tuned within corresponding ranges. The number of piezoelectric elements is accordingly to be selected such that the desired range of adjustment is achieved for the resonance frequency.

The oscillation frequency f, for example of an oscillatory rod, is determined on the basis of its torsional stiffness C at the point of its securement and its mass moment of inertia θ by the formula:

$$f = \sqrt{\frac{C}{\theta}}.$$

Consequently, a change of the stiffness C leads to a change of the oscillation frequency f. Therefore, if the tuning unit is a component of the oscillatable unit or if it is suitably connected with it, then the resonance frequency can be tuned simply and, above all, electrically.

An embodiment provides that the tuning unit is made of a magnetostrictive material whose stiffness is changeable at least by an applied magnetic field. If the tuning unit is a magnetostrictive element, then the application of a magnetic field, preferably a direct-current magnetic-field, through this element leads to a mechanical stress, which in turn leads to a changing of the stiffness of the tuning unit. Magnetostrictive materials are deformable by the application of a magnetic field. Reciprocally, they produce a magnetic field when a mechanical pressure is exerted on them. Classic iron, rare-earth compounds exhibit a higher power density than piezoelectric elements/ceramics. Therefore, they provide many advantages in a number of applications.

An advantageous embodiment includes that a control unit is provided, which electrically controls the tuning unit. Such a control unit evaluates e.g. the oscillations of the oscillatable unit and suitably tunes the resonance frequency. This can be done e.g. via microprocessors. The advantage is that, in this way, in the practical application, an optimizing of the measurement conditions can be automatically performed. The control unit can, however, also be operated e.g. by a user. In the simplest case, the control unit is a controllable resistor by way of which the electrical boundary conditions of the tuning unit, such as e.g. the electrical current between the electrodes, are changed.

An advantageous embodiment provides that the control unit is embodied in such a manner that it tunes the resonance frequency of the oscillatable unit as a function of the oscillation amplitude and/or the oscillation frequency of the mechanical oscillations produced and/or received by the oscillatable unit. Such a control unit can be e.g. a part of the manufactured unit, so that the stiffness is so changed, as a function of the amplitude and/or the frequency, that a predetermined value or e.g. the maximum amplitude is achieved. Such a control unit, for instance, sets a controllable resistance at an appropriate value. This is the application of the invention in the area of manufacture, in order to be able to react to manufacturing tolerances of the components. The control unit can also be a part of the control/evaluation unit, which is most often a component of the apparatus and which there suitably evaluates and also controls the oscillations for determining and/or monitoring the process variable. Thus, the resonance frequency can adjust during the practical application of the apparatus, when this is necessary due to the process conditions. In the case of such an active matching, attention must, however, be paid that a change of the process variable to be monitored or determined is not compensated.

Corresponding embodiments depend in such case on the concrete embodiment of the oscillatable unit and also on the type of application of the apparatus.

The embodiments first to be described are concerned with a so-called single-rod as the oscillatable unit of an apparatus.

An embodiment provides that: In the oscillatable unit, at least one inner oscillatory rod and an outer oscillatory rod are provided; the outer oscillatable rod coaxially surrounds the inner oscillatory rod; the outer and inner oscillatory rods are coupled together; and at least one tuning unit is coupled at least with one of the oscillatory rods. Preferably, the tuning unit is mechanically coupled with at least one of the oscillatory rods or it is connected with at least one of the oscillatory rods. The oscillatory unit is, in this embodiment, a single-rod. See, in this connection, German patent application number 103 18 705. A single-rod serves, for example, for fill level detection, in which case changes of the oscillation amplitude or frequency are interpreted toward determining whether a fill level predetermined by the height of installation is fallen beneath (in which case the transition from covered to free oscillation is determined) or that a fill level is exceeded (in this case it is evaluated how amplitude and frequency react during the transition from "covered" to "free"). In the case of such a single-rod, the inner and outer oscillatory rods must be matched to one another so that no reaction forces and torques occur where the oscillatable unit is secured, so that, thus, no oscillatory energy is lost. Such a matching, which e.g. means equal resonance frequencies of the oscillatory rods, can be lost by accretion or corrosion on the outer oscillatory rod. This can lead to total shutdown. In order to avoid this, the tuning unit of the invention can produce a matching. In this way, it thus becomes possible to react to accretion or corrosion, within a range determined by the embodiment of the tuning unit, in the field, i.e. in the application. The oscillatable unit can, furthermore, also be a so called oscillatory fork such as are manufactured and sold by the assignee under the mark LIQUIPHANT. In such case, then, at least one tine of this fork is to be coupled with a tuning unit.

An advantageous embodiment includes that the tuning unit is at least connected with the inner oscillatory rod. In this way, the tuning unit is protected in the interior of the apparatus and can there optimally provide its correcting service.

An embodiment provides that the control unit is embodied in such a manner that it controls the tuning unit, as a function of the oscillation amplitude, for achieving a maximum amplitude. This is especially relevant for single-rods in the case in which amplitude is used for determining and/or monitoring process variables. In this way, the physical effect utilized for the application is maximized.

The following embodiments relate to an ultrasonic transducer or ultrasonic sensor in a corresponding apparatus. Similar transducers and sensors with other frequency ranges are, however, likewise suited for use in the invention or for putting the invention into practice.

An embodiment includes that: At least one sending/receiving piezo is provided in the oscillatable unit; the tuning unit is a component of the oscillatable unit; and the resonance frequency of the oscillatable unit lies in the ultrasonic range. If the frequencies lie in the ultrasonic range, then the oscillatable unit is an ultrasonic transducer. Such a transducer can be operated continuously or produce so called bursts or wave packets. In the simplest construction, the sending/receiving piezo sends and receives alternately, as required. If a plurality of piezoelectric elements is provided in the oscillatable unit, then one of these elements can be the tuning unit.

One embodiment for the area of ultrasonic oscillations includes that: At least one front-side mass and one rear-side mass are provided in the oscillatable unit; at least one sending/receiving piezo is provided between the two masses; at least one tuning unit is a component of one of the two masses; and the resonance frequency of the oscillatable unit lies in the ultrasonic range. The oscillatable unit is in this second embodiment, thus, an ultrasonic transducer or ultrasonic sensor of the Langevin-type. The resonance frequency is, in such case, usually inversely proportional to the length of the total unit formed of the 2 masses and the sending/receiving piezo, since the half wave length corresponds to this length. This condition can, however, be changed by changing the velocity of sound in at least one of the two masses, and it is here that also the great advantage of the invention is achieved. If at least one tuning unit is a component of at least one mass, then, by changing the stiffness, also the velocity of sound in this mass can be changed. In this way, a much easier matching of the resonance frequency is possible as compared e.g. to a shortening or lengthening of the masses. This tuning unit is, therefore, especially relevant for being able to react to manufacturing tolerances. Furthermore, in this way, the sensor can also be tuned to a desired frequency range without having to use an, otherwise, usual damper, which most often leads to a reduction of the power since it makes the sensor broadbanded. It is also possible, in this way, that the ultrasonic transducer is tunable with full power at a plurality of resonance frequencies. The invention is, however, also in this area, not limited to the application in the ultrasonic range.

An advantageous embodiment provides that at least one matching layer is provided in the oscillatable unit for coupling to the medium. In order to assure maximum effectiveness in certain media (e.g. water), a $\lambda/4$ matching layer is often used. Such matching layers have, however, usually another temperature dependence of the velocity of sound as compared to the piezo resonator. Therefore, at certain temperatures the power drops. With the tuning unit of the invention, it is possible to provide a matching of the resonance frequency to the λ/4 matching layer for a wide temperature range. The resonance frequency can, thus, be matched to the matching layer upon temperature changes via the tuning unit of the invention.

An advantageous embodiment includes that at least one bolt is provided in the oscillatable unit for producing a prestress. The connection between the two masses and the sending/receiving piezo can be accomplished by adhesives or by a bolt. The power of the ultrasonic sensor depends on the mechanical prestress between the parts. This prestress is defined via the bolt. If the bolt is loosened, the prestress goes down and also the power. In the sense of predictive maintenance, there is the question of how this prestress can be checked without having to unscrew the unit. Such a capability would allow timely recognition of loss of the prestress without having to remove the measuring apparatus from the installed state. The invention makes possible thus a direct checking in the field. When the ultrasonic sensor is made of different components of different stiffness, then usually the smallest occurring stiffness is dominant. With the tuning unit of the invention, however, it is possible to vary the stiffness without changing the prestress. By this change, a certain influence on the resonance frequency of the structure results provided that the sensor itself does not deviate too much from the stiffness of the tuning unit. If the mechanical prestress is reduced, then, however, also the frequency change by the changing of the stiffness is reduced, because the total stiffness is defined more strongly by the loosened bolt. In this way, it is possible to deduce, from the deviating from the known frequency change, that the bolt has loosened.

An embodiment of the apparatus of the invention provides that the oscillatable unit includes at least one measuring tube of a measurement pickup of vibration-type inserted into the course of a pipeline, especially a Coriolis mass flow or a Coriolis mass flow/density meter. Such principles of measurement are disclosed in the documents U.S. Pat. No. 5,796,011, U.S. Pat. No. 6,651,513, U.S. Pat. No. 6,006,609 or U.S. Pat. No. 5,531,126.

The object of the invention relates also to a method for changing the resonance frequency of an apparatus for determining and/or monitoring at least one physical or chemical, process variable of a medium with at least one oscillatable unit, which produces and/or receives mechanical oscillations. The term "resonance frequency of an apparatus" means, in such case, the resonance, or, in general, the oscillation, frequency with which the measuring apparatus works, thus determines and/or measures, the corresponding process variable.

The object is achieved with reference to the method of the invention by changing the stiffness of at least one tuning unit, which is connected with the oscillatable unit or is a component of the oscillatable unit. If the oscillatable unit is an oscillatable system whose resonance frequency is determined by the stiffness of at least one component, then for example, a piezoelectric unit enables a simple and above all electrically controllable tuning of the resonance frequency. Additionally, the embodiments for the above described apparatus of the invention can also be applied for the method.

BRIEF DESCRIPTION OF THE DRAWINGS

The invention will now be explained in greater detail on the basis of the appended drawings, the figures of which show as follows:

FIG. 1 an apparatus whose oscillatory rods are shown in section; and

FIG. 2 an ultrasonic sensor equipped with a tuning unit of the invention.

DESCRIPTION OF THE PREFERRED EMBODIMENTS

FIG. 1 shows an apparatus 1, in the case of which the oscillatable unit 5 is a single-rod 10 composed of an inner oscillatory rod 10.1 and an outer oscillatory rod 10.2. In such case, the outer oscillatory rod 10.2 coaxially surrounds the inner oscillatory rod 10.1. Both oscillatory rods 10.1, 10.2 are elastically coupled together via a first membrane 11.1. The outer oscillatory rod 10.2 is connected securely with the process connection 12 via a second membrane 11.2. Via this process connection, the apparatus 1 is installed in a container (not shown), in order e.g. to monitor the fill level of a medium (here, especially, a bulk good) in this container. Via the driving/receiving piezo 13, the oscillatory rods 10.1, 10.2 are excited to oscillate with opposite phase. For this, it is necessary that both oscillatory rods 10.1, 10.2 have the same resonance frequency. If the outer oscillatory rod 10.2 comes into contact with the bulk good, an amplitude change results since the single-rod 10 looses energy due to frictional effects. The same holds when the outer oscillatory rod 10.2 is first covered and then subsequently oscillates freely. The changes of the amplitude are usually converted into corresponding reports.

Important is that energy not be lost from the single-rod 10 due to the fact e.g. that, by an incorrect matching of the two oscillatory rods 10.1, 10.2, energy is transmitted to the process connection 12 and, thus, to the container. This means that the radial force at the center of gravity of the inner oscillatory rod 10.1 must be essentially the same as that of the outer oscillatory rod 10.2 and that the torques on the securement have also to be essentially equal. The forces and torques should, thus, exactly cancel essentially in the region of the process connection, due to the oscillations of opposite phase. Therefore, a tuning of the two oscillatory rods 10.1, 10.2 to one another is required. If such an oscillatory system is optimally balanced, then it can be used in the practice. A further problem, however, is that by contact with the medium, accretions can form, or corrosion can occur, on the outer oscillatory rod 10.2. In this way, the mass of the outer oscillatory rod 10.2 changes and consequently another mass moment of inertia results and thereby also another oscillation frequency and other oscillation amplitudes for the outer oscillatory rod 10.2. In this way, however, the inner oscillatory rod 10.1 and the outer oscillatory rod 10.2 are no longer tuned to one another and oscillation energy is transmitted to the process connection 12. Therefore, here, in the case of accretion or corrosion, the tuning unit 20 of the invention becomes important.

The tuning unit here is made of a piezoelectric material on which two electrodes 21 are connected. Depending on whether the electrodes 21 are free or short-circuited, i.e. whether an electric current can flow or not, the stiffness of the piezoelectric element 20 changes. Between a short-circuited piezoelectric element 20 and one connected with a constant voltage, one achieves in the case of this element, percentage stiffness changes which lie in the range of up to 25%. The tuning unit 20 is controlled by a control unit 25 whose deciding element in the simplest embodiment is a controllable resistor. Connected therewith is then, for example, a corresponding control electronics e.g. having a microprocessor control (not shown). Via the resistance of the control unit 25, the piezoelectric element 20 can then be gradually short-circuited, with the stiffness concurrently declining. In this way, the stiffness of the piezoelectric element and, consequently, that of the inner oscillatory rod 10.1 can be gradually reduced. Thereby, the resonance frequency changes and it is possible essentially to rebalance the two oscillatory rods 10.1, 10.2, in spite of the accretion or in spite of the corrosion, so that essentially no forces or torques act on the securement 12 and that consequently the single-rod 10 again exhibits an optimum sensitivity. In the case of the correcting carried out according to the invention, it is, however, always to be assured that the measured effects are not canceled out without their being used for determining the measured variable. The oscillatable unit can also be a so-called oscillatory fork. In such case, the two tines contact the medium.

FIG. 2 shows an ultrasonic transducer 15, which is part of an apparatus 1 for determining and/or monitoring a process variable, e.g. a fill level. Using the travel time method, such an ultrasonic transducer 15 can be used to determine, for example, the fill height of a medium. To accomplish this, waves are emitted and detected and, from their travel time, the distance to the reflecting surface is determined. The ultrasonic transducer can serve e.g. as an electroacoustic transducer of a fill level measuring device or an ultrasonic flow measuring device for a fluid flowing in a pipeline.

The ultrasonic transducer 15 is composed of a front-side mass 15.1 and a rear-side mass 15.2 and a sending/receiving piazzo 16 between these two masses 15.1 and 15.2. A bolt 18 cares for the appropriate prestress, by way of which the power of the ultrasonic transducer 15 results. The resonance frequency of the ultrasonic transducer 15 is inversely proportional to its length, to the extent that there are not different velocities of sound present therein. On the front-side mass 15.1, there is a matching layer 17, which is, for example, a $\lambda/4$ layer for coupling to certain media, e.g. water. The tuning unit 20 is here a part of the rear-side mass 15.2 and can consequently tune there, via the stiffness change, the velocity of sound in the rear-side mass 15.2 and in this way the resonance frequency of the oscillatable unit 5, or the ultrasonic transducer 15, as the case may be. The tuning unit 20 can, in the case of such an ultrasonic transducer 15, as oscillatable unit 5, fulfill multiple responsibilities. On the one hand, in this way, manufacturing tolerances can be reacted to, by suitably readjusting the resonance frequency. Furthermore, in this way, an ultrasonic transducer can be manufactured, which works at different frequencies, without it coming to losses of power due to a damper. This power loss results from the fact that the damper makes the ultrasonic transducer 15 broadbanded. Furthermore, it also becomes possible to react to resonance changes in the matching layer 17 due to temperature influences. The temperature behavior of such a $\lambda/4$ matching layer 17 usually differs from that of the ultrasonic transducer 15. Thereby, it can, however, come to a situation in which the ultrasonic transducer 15 and the matching layer 17 are no longer matched, with this usually being connected with power losses. And, beyond this, by known changing of the stiffness, the prestress of the bolt can be reviewed. If, at a given prestress, the frequency change of the ultrasonic transducer as a result of a change of the stiffness of the tuning unit 20 is known, then it is possible to deduce, in the case of deviations therefrom, the presence of a reduced prestress.

The invention claimed is:

1. An apparatus for determining and/or monitoring the fill level, density and/or viscosity of a medium in a container, comprising:
   at least one oscillatable unit which produces, and/or receives, mechanical oscillations;
   at least one tuning unit whose stiffness is variable and which is embodied in such a manner and connected in such a manner with said oscillatable unit, or is a component of said oscillatable unit in such a manner, that at least the resonance frequency of said oscillatable unit is changeable via said at least one tuning unit; and
   at least one inner oscillatory rod and an outer oscillatory rod provided in said oscillatable unit, wherein:
   said outer oscillatory rod surrounds said inner oscillatory rod coaxially;
   said outer oscillatory rod and said inner oscillatory rod are coupled together; and
   said at least one tuning unit is coupled at least with one of said oscillatory rods.

2. The apparatus as claimed in claim 1, wherein:
   said tuning unit comprises a piezoelectric material, which is connected with electrodes and whose stiffness is changeable at least by an electric current between the electrodes.

3. The apparatus as claimed in claim 1, wherein:
   said tuning unit comprises a magnetostrictive material whose stiffness is changeable at least by an applied magnetic field.

4. The apparatus as claimed in claim 1, further comprising:
   a control unit which controls said tuning unit electrically.

5. The apparatus as claimed in claim 4, wherein:
   said control unit is embodied in such a manner that it tunes the resonance frequency of said oscillatable unit as a function of the oscillation amplitude and/or oscillation frequency of the mechanical oscillations produced and/or received by said oscillatable unit.

6. The apparatus as claimed in claim 1, wherein:
   said tuning unit is connected at least with said inner oscillatory rod.

* * * * *